(12) United States Patent
Ohnogi et al.

(10) Patent No.: US 7,361,774 B2
(45) Date of Patent: Apr. 22, 2008

(54) CHALCONE COMPOUND

(75) Inventors: Hiromu Ohnogi, Kusatsu (JP); Katsumi Sugiyama, Otsu (JP); Nobuko Muraki, Koka (JP); Tatsuji Enoki, Kyotanabe (JP); Hiroaki Sagawa, Kusatsu (JP); Ikunoshin Kato, Koka (JP)

(73) Assignee: Takara Bio Inc., Otsu-Shi (JP)

( * ) Notice: Subject to any disclaimer, the term of this patent is extended or adjusted under 35 U.S.C. 154(b) by 359 days.

(21) Appl. No.: 10/529,859

(22) PCT Filed: Sep. 29, 2003

(86) PCT No.: PCT/JP03/12381

§ 371 (c)(1),
(2), (4) Date: Mar. 31, 2005

(87) PCT Pub. No.: WO2004/031165

PCT Pub. Date: Apr. 15, 2004

(65) Prior Publication Data

US 2005/0272809 A1    Dec. 8, 2005

(30) Foreign Application Priority Data

Oct. 1, 2002   (JP) .............................. 2002-289050

(51) Int. Cl.
C07D 311/82   (2006.01)
C07D 311/00   (2006.01)
A01N 43/16    (2006.01)

(52) U.S. Cl. ................. 549/388; 549/399; 549/405; 514/457

(58) Field of Classification Search ........... 549/399, 549/405, 388
See application file for complete search history.

(56) References Cited

FOREIGN PATENT DOCUMENTS

| EP | 1254658 A1 | 11/2002 |
|---|---|---|
| JP | 63-104912 A | 5/1988 |
| JP | 7-165588 A | 6/1995 |
| JP | 2000-72766 A | 3/2000 |
| JP | 2001-58969 A | 3/2001 |
| WO | WO-02/49632 A1 | 6/2002 |

OTHER PUBLICATIONS

Parmar et al., "Anti-invasive activity of alkaloids and polyphenolics in vitro", Bioorganic & Medicinal Chemistry, 1997, vol. 5, No. 8, pp. 1609-1619.

Yook et al., "Alkylation of orcinol with nerol in modified lewis acid", Bulletin of the Korean Chemical Society, 1992, vol. 13, No. 5, pp. 457-458.

J.R. Dimmock et al.; Current Medicinal Chemistry, 1999, No. 6; pp. 1125-1149.

*Primary Examiner*—Janet L. Andres
*Assistant Examiner*—Raymond Covington
(74) *Attorney, Agent, or Firm*—Birch, Stewart, Kolasch & Birch, LLP (57) ABSTRACT

The present invention relates to a chalcone compound represented by the following general formula:

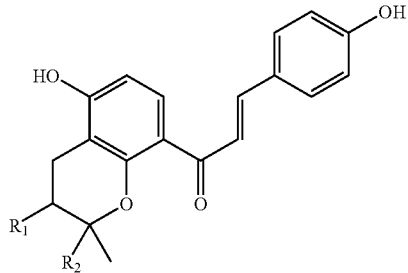

wherein $R_1$ and $R_2$ are taken together with the carbon atom to which they are bound, respectively, to form a hydroxy-dimethyl hexane ring, or where $R_1$ is a hydroxyl group, $R_2$ is an isohexenyl group, a derivative thereof, or a salt thereof. Also, the present invention relates to a therapeutic agent or prophylactic agent for a disease requiring neuronal protection, suppression for nitrogen monoxide (NO) production, inhibition for aldose reductase or suppression for interleukin production, and a food, beverage or feed for treatment or prevention of the above-mentioned disease, characterized in that each comprises the above-mentioned compound as an effective ingredient.

5 Claims, 8 Drawing Sheets

CHALCONE COMPOUND

TECHNICAL FIELD

The present invention relates to a novel chalcone compound, and a medicament, foodstuff and the like, utilizing the physiological action of the compound.

BACKGROUND ART

Chalcone compounds are collective name of compounds having the chalcone backbone of the following formula. As these compounds, various compounds obtained by extraction from natural products or synthesis have been known.

In addition, as to the physiological activities for these compounds, there are a variety of physiological activities depending upon the compound. For example, cytotoxicity, anticancer activity, chemical defense, anti-mutagenesity, anti-bacterial activity, antiviral activity, antiprotozoal activity, insecticidal action and the like have been known (for example, see J. R. Dimmock and three others, *Current Medicinal Chemistry*, (the Netherlands), 1999, 6, 1125-1149). Also, the present inventors have found that these chalcone compounds have enhancing actions for nerve growth factor (NGF) production (see, for example, WO 01/54682).

DISCLOSURE OF INVENTION

An object of the present invention is to provide a novel chalcone compound, and a medicament, foodstuff and the like, utilizing the physiological action of the compound.

Summarizing the present invention, a first invention of the present invention relates to a compound represented by the following general formula (1):

(1)

wherein $R_1$ and $R_2$ are taken together with the carbon atom to which they are bound, respectively, to form a hydroxydimethyl cyclohexane ring, or where $R_1$ is a hydroxyl group, $R_2$ is an isohexenyl group,
a derivative thereof, or a salt thereof.

A second invention of the present invention relates to a therapeutic agent or prophylactic agent for a disease sensitive to the compound as defined in the first invention of the present invention, characterized in that the agent comprises the compound as an effective ingredient. In the second invention of the present invention, the disease sensitive to the compound is exemplified by a disease requiring neuronal protection, suppression for nitrogen monoxide (NO) production, inhibition for aldose reductase or suppression for interleukin production.

A third invention of the present invention relates to a neuronal protection agent, a suppressive agent for NO production, an inhibitory agent for aldose reductase or a suppressive agent for interleukin production, characterized in that the agent comprises the compound as defined in the first invention of the present invention as an effective ingredient.

A fourth invention of the present invention relates to a food, beverage or feed for treatment or prevention of a disease requiring neuronal protection, suppression for nitrogen monoxide (NO) production, inhibition for aldose reductase or suppression for interleukin production, characterized in that the food, beverage or feed comprises the compound as defined in the first invention of the present invention as an effective ingredient.

BRIEF DESCRIPTION OF THE DRAWINGS

FIG. 1 is a mass spectrum of a compound a.
FIG. 2 is a $^1$H-NMR spectrum of the compound a.
FIG. 3 is a $^{13}$C-NMR spectrum of the compound a.

BEST MODE FOR CARRYING OUT THE INVENTION

The present inventors have found a novel chalcone compound derived from an edible plant represented by the above-mentioned general formula (1), a derivative thereof or a salt thereof (hereinafter referred to as the compound of the present invention), and a neuronal protection action, a suppressive action for NO production, an inhibitory action for aldose reductase or a suppressive action for interleukin production owned by the compound, thereby making it possible to provide a medicament, foodstuff or feed, comprising the compound as an effective ingredient. Here, the compound of the present invention is exemplified by (E)-1-(5,6,7,8,8a,10a-hexahydro-1,7-dihydroxy-8,8,10a-trimethyl-9H-xanthen-4-yl)-3-(4-hydroxyphenyl)-2-propen-1-one represented by the following formula (A):

(A)

and (E)-1-(3,4,-dihydro-3,5-dihydroxy-2-(3-isohexeneyl)-2-methyl-2H-1-benzopyran-8-yl)-3-(4-hydroxyphenyl)-2-propene-1-one represented by the following formula (B):

(B)

The compound of the present invention which is usable as an effective ingredient in the present invention may be a naturally derived product, or a synthetic product or semi-synthetic product. The naturally derived product is preferably those derived from an edible plant, and the edible plant is exemplified by *Angelica keiskei* koidz., which is a plant belonging to Umbelliferae. In addition, when various isomers of the compound of the present invention are present, any of them can be arbitrarily used in the present invention. The compound of the present invention can be used alone or in admixture of two or more kinds.

The derivative of the compound represented by the above-mentioned general formula (1) as used herein refers to a compound prepared by using the compound as an original compound, wherein the compound has a similar action to the compound represented by the general formula (1), i.e., a neuronal protection action, a suppressive action for NO production, an inhibitory action for aldose reductase or a suppressive action for interleukin production. The derivative includes, for instance, a compound capable of being easily hydrolyzed in a body to exhibit the desired effects (prodrug), such as an ester form, an ether form, or a glycoside form of the compound represented by the above-mentioned general formula (1). The prodrug may be prepared in accordance with a known method. The derivative may be a salt thereof.

In addition, in the compound of the present invention, as the salt, a pharmacologically acceptable salt is preferable. The salt usable in the present invention is exemplified by alkali metal salts, alkaline earth metal salts, salts with an organic base and the like. As the salt, a pharmacologically acceptable salt is preferable. Here, the pharmacologically acceptable salt means a salt which is substantially nontoxic against an organism. The salts include, for instance, salts with sodium, potassium, calcium, magnesium, ammonium or protonated benzathine (N,N'-di-benzylethylenediamine), choline, ethanolamine, diethanolamine, ethylenediamine, meglamine (N-methylglucamine), benethamine (N-benzylphenetylamine), piperazine or tolomethamine (2-amino-2-hydroxymethyl-1,3-propanediol).

The compound of the present invention which is naturally derived can be prepared by a combination of known preparation methods. For instance, the compound can be purified from a substance containing the compound represented by the above-mentioned general formula (1), for instance, a plant such as *Angelica keiskei* koidz. As the purification means, there may be employed a known purification means such as chemical method or physical method, and conventionally known purification methods such as gel filtration, fractionation method with a molecular weight fractionation membrane, solvent extraction method, and various chromatographic methods using ion exchange resins and the like may be combined to purify the compound of the present invention. For instance, the compound of the present invention can be prepared by referring to Examples 1 and 2 set forth below.

Also, for instance, a semi-synthesized product is obtained by subjecting a chalcone compound derived from a natural product as a raw material to organic synthesis, and a synthetic product is obtained by entirely carrying out organic synthesis. The method of organic synthesis may be, for instance, referred to Alessandra Lattanzi et al., *Synlett.* 2002, No. 6, p 942-946; L. Claisen A. et al., *Ber.* 1881, No. 14, p 2460; and the like.

According to the present invention, there is provided a therapeutic agent or prophylactic agent for a disease sensitive to the compound of the present invention, wherein the agent comprises the compound as an effective ingredient. The disease sensitive to the compound refers to a disease for which therapeutic effects or prophylactic effects can be obtained by the compound. The disease includes, for instance, a disease requiring neuronal protection, suppression for NO production, inhibition for aldose reductase or suppression for interleukin production.

The brain functional disorder accompanying neuronal deaths is understood as main causations for many of central degenerative diseases such as apoplexy, senile dementia, Alzheimer's disease, Huntington's disease, Parkinson's disease, and cerebral ischemia. As the mechanism for neuronal deaths observed in these diseases, glutamic acid-$Ca^{2+}$—NO hypothesis has been suggested. And the role of NO has been remarked as a mediator of the neuronal deaths.

Since the compound of the present invention has neuronal protection action (suppressive action for NO toxicity) from a NO donor as described in Example 4, the compound is useful for a disease requiring neuronal protection. The above-mentioned disease requiring the neuronal protection is exemplified by, for instance, diseases such as apoplexy, senile dementia, Alzheimer's disease, Huntington's disease, Parkinson's disease, and cerebral ischemia.

Vascularization is essential for an increase in solid cancer, and vascular endothelial growth factor/vascular permeability-enhancing factor (VEGF) plays a key role in this process. VEGF in various cancerous cells is induced by NO. In other words, the VEGF production is suppressed by suppressing the NO production of the cancerous cells, thereby resulting in inhibition of vascularization in the surrounding of the cancerous cells, whereby cancer can be necrotized.

In addition, NO reacts with an amine under the physiological conditions of a neutral pH to generate a nitrosoamine. This nitrosoamine has been known to show carcinogenicity by damaging DNA. Also, NO production is enhanced in a patient infected with *Clonorchis sinensis* or a patient suffering from cirrhosis, which has immunologically high association with cancer. Therefore, carcinogenesis of a high-risk group can be prevented by suppressing NO production.

NO also induces an edema characteristically found in an inflammatory lesion, in other words, enhancing action for vascular permeability [*Japanese Journal of Cancer Research,* 85, 331-334 (1994)], or enhances biosynthesis of a prostaglandin, which is an inflammatory mediator [*Proceedings of the National Academic of Sciences of the USA,* 90, 7240-7244 (1993)]. On the other hand, NO rapidly reacts with a superoxide radical to generate a peroxynitrite ion, and the peroxynitrite ion is considered to cause an inflammatory cell or a tissue disorder.

In addition, in a synovial fluid of a lesion portion of a patient suffering from arthritis such as chronic rheumatoid arthritis, rheumatic osteoarthritis, gouty arthritis, or Behcet's disease, NO at a high concentration is contained as compared to a synovial fluid of normal articulation of the same patient or an articulation of a normal individual.

Since the compound of the present invention has a suppressive action for NO production as described in Example 5, the compound is useful for the carcinogenetic diseases and the inflammatory diseases mentioned above. The disease requiring suppression for NO production for which the compound of the present invention is effective includes diseases such as carcinogenetic diseases, inflammatory diseases, chronic rheumatic arthritis, rheumatic osteoarthritis, gouty arthritis, and Behcet's disease.

The aldose reductase (hereinafter referred to as AR in some cases) is an enzyme involved in a polyol pathway, which is one of the glucose metabolism pathways in a living body. The pathway comprises a reducing pathway from glucose to sorbitol in which AR is involved, and a dehydrogenation reaction pathway from sorbitol to D-fructose in which sorbitol dehydrogenase (hereinafter referred to as SDH in some cases). If the amount of glucose allowed to flow into a cell is increased, the glucose which cannot be treated with a glycolytic pathway enhances the polyol pathway. However, since the SDH activity is lower than the AR activity, sorbitol, which is an intermediate metabolite, is produced in a large amount if the glucose is allowed to flow continuously. As to various diseases caused by accumulation of sorbitol as mentioned above, in other words, diseases which are onset as diabetic complications, there have been known, for instance, diseases such as cataract, peripheral nerve diseases, nephritic diseases, infections caused by lowering of phagocytotic action of leukocytes, diabetic coma, and arteriosclerosis caused by atheromatous degeneration in the great vessel wall.

Since the compound of the present invention has an inhibitory action for AR as described in Example 3, the compound is useful for the diabetic complications mentioned above. The disease requiring inhibition for AR for which the compound of the present invention is effective is exemplified by, for instance, diseases such as cataract, peripheral nerve diseases, nephritic diseases, infections caused by lowering of phagocytotic action of leukocytes, diabetic coma, and arteriosclerosis caused by atheromatous degeneration in the great vessel wall. Also, the compound of the present invention can be used together with other therapeutic agents for diabetes.

Interleukins are a collective name for protein physiologically active substances for producing lymphocytes and monocytes, and the existence of interleukin-1 to −25 have been known. Interleukin 6 (hereinafter referred to as IL-6 in some cases) is a factor for inducing the final differentiation process of B cell, and is involved not only in immune responses but also in the cell differentiation and acute reactions in the hematopoietic system and the nervous system, and further has a close association with the onset of various immune disorders, inflammatory diseases and lymphatic tumors. In addition, IL-6 induces B cell to produce antibody, so that immunoglobulin of each of classes of IgM, IgG and IgA is produced. However, unlike IL-4, IL-6 is not involved in class switches. IL-6 also functions as a growth factor for B cell and plasmacyte. On the other hand, IL-6 is involved in T cell system to proliferate or differentiate T cell.

IL-6 is also involved in the hematopoietic system, and IL-6 shortens the G0 phase in cooperation with IL-3, thereby proliferating hematopoietic stem cell. IL-6 also promotes megakaryocyte maturation to induce an increase in platelet count. IL-6 is involved in acute reactions in which a living body responds immediately to a bacterial or viral infection, a malignant tumor, or the like. IL-6 is also involved in the nervous system, in which IL-6 is secreted from nervous system cell such as glioblastoma or astrocytoma, and functions in the induction of differentiation of the nervous system.

In chronic rheumatoid arthritis or systemic lupus erythematosus, activation of B cells is found, and IL-6 has been known to be present in a high concentration in a synovial fluid of the patient suffering therefrom. Also, in Castleman's syndrome characterized by systemic articular enlargement, the IL-6 concentration in blood has been known to be very high. In addition, in a patient suffering from atrial myxoma showing autoimmune disease, a large amount of IL-6 has been known to be produced from tumor cells. Additionally, there has been known that IL-6 is highly possibly a self growth factor for myeloma cells because the proliferation of the myeloma cells derived from a patient suffering from multiple myeloma is suppressed by an anti-IL-6 antibody. Further, IL-6 is contained in urine of a patient suffering from primary glomerular nephritis, and IL-6 has been known to act as a growth factor for nephritic mesangial cells.

Since the compound of the present invention has a suppressive action for IL-6 production as described in Example 6, the compound is useful for the disease requiring suppression for IL-6 production. The disease requiring suppression for IL-6 production for which the compound of the present invention is effective is exemplified by, for instance, diseases such as chronic rheumatoid arthritis, systemic lupus erythematosus, anomaly of B cells, Castleman's syndrome, autoimmune diseases, atrial myxoma, multiple myeloma, primary glomerular nephritis, mesangial cell-growing glomerular nephritis, plasmacytoma, myeloma, and acquired immunodeficiency syndrome (AIDS).

The therapeutic agent or prophylactic agent of the present invention mentioned above comprises the compound of the present invention as an effective ingredient, and can be manufactured by combining the compound with a known pharmaceutical carrier. In general, these compounds are formulated with a pharmacologically acceptable liquid or solid carrier, and a solvent, a dispersant, an emulsifier, a buffer, a stabilizer, an excipient, a binder, a disintegrant, a lubricant, or the like is optionally added thereto, so that a solid agent such as a tablet, a granule, a powder, a fine powder, and a capsule, or a liquid agent such as a common liquid agent, a suspension agent or an emulsion agent can be formed. In addition, there can be also made into a dry product which can be made liquid by adding an appropriate liquid carrier before use.

The pharmaceutical carrier can be selected depending upon the administration form and preparation form of the therapeutic agent or prophylactic agent. In the case of an orally administered preparation comprising a solid composition, the preparation can be produced in the form of a tablet, a pill, a capsule, a powder, a fine powder, a granule or the like, and there can be utilized, for instance, starch, lactose, saccharose, mannitol, carboxymethyl cellulose, cornstarch, an inorganic salt or the like. In addition, during the preparation of the orally administered preparation, a binder, a disintegrant, a surfactant, a lubricant, a fluidity accelerator, a flavor, a colorant, a perfume, and the like can be further formulated. In the case of forming into a tablet or pill, for instance, the tablet or pill may be covered with a sugar-coating made of sucrose, gelatin or hydroxypropyl cellulose, or with a film made of a substance soluble in the stomach or intestine as desired. In the case of an orally administered preparation comprising a liquid composition, the preparation can be prepared in the form of a pharmaceutically acceptable emulsion, solution, suspension, syrup, or the like. In this case, for instance, purified water, ethanol or the like is utilized as a carrier. Furthermore, an auxiliary agent such as a wetting agent or a suspending agent, a sweetener, a flavor, an antiseptic, or the like may be added as desired.

On the other hand, in the case of a non-orally administered preparation, the preparation can be prepared by dissolving or suspending the above-mentioned effective ingredient of the present invention in a diluent such as distilled water for injection, physiological saline, an aqueous solution of glucose, vegetable oil for injection, sesame oil, peanut oil, soybean oil, corn oil, propylene glycol or polyethylene glycol, in accordance with a conventional method, and adding a microbicide, a stabilizer, an osmotic regulator, a soothing agent, or the like as desired. It is also possible to produce a solid composition which is dissolved in sterile water or a sterile solvent for injection before use.

The external preparation includes solid, semi-solid or liquid preparations for percutaneous administration or transmucosal (oral or intranasal) administration. The external preparation also includes suppositories and the like. For instance, the external preparation may be prepared as liquid preparations including emulsions, suspensions such as lotions, external tinctures, and liquid agents for transmucosal administration; ointments such as oily ointments and hydrophilic ointments; medical adhesives for percutaneous administration or transmucosal administration such as films, tapes and poultices; and the like.

Each of the above-mentioned various preparations can be appropriately produced in accordance with conventional methods by utilizing known pharmaceutical carriers and the like. Also, the content of the effective ingredient in the preparation is not particularly limited, as long as the content is in an amount so that the effective ingredient can be preferably administered within the dose range described below in consideration of administration form, administration method and the like of the preparation.

The content of the above-mentioned effective ingredient in the therapeutic agent or prophylactic agent of the present invention is not particularly limited. The content is exemplified by usually from 0.001 to 80% by weight, preferably from 0.01 to 50% by weight, especially preferably from 0.1 to 20% by weight.

The dose of the therapeutic agent or prophylactic agent of the present invention is changeable and properly set depending upon its preparation form, administration method, purpose of use, and age, body weight, symptom or the like of a patient to which the agent is applied, or the like. Generally, the dose of the agent, in terms of the dose of the effective ingredient contained in the preparation, is from 10 μg to 1 g/kg weight, preferably from 50 μg to 500 mg/kg weight, more preferably from 100 μg to 100 mg/kg weight, for human (for instance, adult) per day. As a matter of course, the dose varies depending upon various conditions, so that an amount smaller than the dose mentioned above may be sufficient, or an amount exceeding the dose range may be required. The agent of the present invention can be directly orally administered, or the agent can be added to any foodstuff to be taken on a daily basis.

In addition, the present invention can provide a neuronal protection agent, a suppressive agent for NO production, an inhibitory agent for aldose reductase or a suppressive agent for interleukin production, wherein the agent comprises the compound of the present invention as an effective ingredient. The neuronal protection agent, the suppressive agent for NO production, the inhibitory agent for aldose reductase or the suppressive agent for interleukin production of the present invention may be the above-mentioned effective ingredient itself, or a composition comprising the above-mentioned effective ingredient. In the embodiment of the present invention, the salt as the effective ingredient is preferably a pharmacologically acceptable salt. The neuronal protection agent, the suppressive agent for NO production, the inhibitory agent for aldose reductase or the suppressive agent for interleukin production of the present invention may be prepared by, for instance, formulating the above-mentioned effective ingredient with other ingredients which can be used for the same application as the effective ingredient, and forming into a form of reagent usually used according to the above-mentioned process for preparing the therapeutic agent or prophylactic agent. The content of the above-mentioned effective ingredient in the neuronal protection agent, the suppressive agent for NO production, the inhibitory agent for aldose reductase or the suppressive agent for interleukin production of the present invention is not particularly limited, as long as the content is in an amount so that the desired effects of the present invention can be exhibited in consideration of administration method, purpose of use or the like of the agent. The content of the effective ingredient is exemplified by usually from 0.001 to 100% by weight, preferably from 0.01 to 80% by weight, especially preferably from 0.1 to 80% by weight. Also, the amount of the agent used is not particularly limited, as long as the desired effects of the present invention can be exhibited. Especially in the case where the agent is administered to a living body, the agent may be preferably used in an amount so that the effective ingredient can be administered within the dose range of the effective ingredient for the above-mentioned therapeutic agent or prophylactic agent. The neuronal protection agent, the suppressive agent for NO production, the inhibitory agent for aldose reductase or the suppressive agent for interleukin production of the present invention is useful in a disease requiring neuronal protection, suppression for NO production, inhibition for aldose reductase or suppression for interleukin production for the treatment or prevention. In addition, the neuronal protection agent, the suppressive agent for NO production, the inhibitory agent for aldose reductase or the suppressive agent for interleukin production of the present invention is also useful for screening of drugs for these diseases. Furthermore, the neuronal protection agent, the suppressive agent for NO production, the inhibitory agent for aldose reductase or the suppressive agent for interleukin production of the present invention is useful for functional studies relating to physical changes in these diseases.

The foodstuff or feed of the present invention comprises the above-mentioned effective ingredient. In other words, the present invention provides a food, beverage or feed in which the compound of the present invention is contained, added and/or diluted. Since the foodstuff or feed has a neuronal protection action, a suppressive action for NO production, an inhibitory action for aldose reductase or a suppressive action for interleukin production, the foodstuff or feed is very useful in amelioration of symptoms or prevention for a disease requiring neuronal protection, suppression for NO production, inhibition for aldose reductase or suppression for interleukin production for the treatment or prevention.

As used herein, the above-mentioned term "containing (ed)" refers to an embodiment of containing the effective ingredient usable in the present invention in the food, beverage or feed; the above-mentioned term "adding(ed)" refers to an embodiment of adding the effective ingredient usable in the present invention to a raw material for the food, beverage or feed; and the above-mentioned term "diluting (ed)" refers to an embodiment of adding a raw material for the food, beverage or feed to the effective ingredient usable in the present invention.

The process for preparing the food, beverage or feed of the present invention is not particularly limited. A generally used process for preparing a food, beverage or feed can be employed, as long as the resulting food, beverage or feed may contain the compound of the present invention as the effective ingredient in a high content, wherein the content is higher than that of a usual foodstuff or feed. The expression "contained . . . in a high content" as used herein means that the weight of the compound of the present invention per unit weight of the food, beverage or feed of the present invention is larger than the weight of the compound of the present invention per unit weight of the raw material, for instance, *Angelica keiskei* koidz., for the effective ingredient of the present invention.

The food or beverage of the present invention is not particularly limited. The food or beverage includes, for instance, processed agricultural and forest products, processed stock raising products, processed marine products and the like, including processed grain products, processed fat and oil products, processed soybean products, processed meat products, marine products, milk products, processed vegetable and fruit products, confectionaries, alcohol beverages, luxury drinks, seasonings, canned, binned or pouched foods, semi-dry or concentrated foods, dry foods, frozen foods, solid foods, liquid foods, spices, and the like.

In the food or beverage of the present invention, the above-mentioned effective ingredient is contained, added and/or diluted, alone or in plurality, and its shape is not particularly limited, as long as the effective ingredient is contained in an amount necessary for exhibiting its neuronal protection action, suppressive action for NO production, inhibitory action for aldose reductase or suppressive action for interleukin production. For instance, the shape includes those which can be taken orally such as tablets, granules and capsules.

The content of the above-mentioned effective ingredient in the food or beverage of the present invention is not particularly limited, and the content can be appropriately selected from the viewpoints of sensory aspect and exhibition of activity. The content of the effective ingredient is, for instance, preferably 0.00001% by weight or more, more preferably from 0.0001 to 10% by weight, even more preferably from 0.0006 to 6% by weight, per 100% by weight of the food. The content is, for instance, preferably 0.00001% by weight or more, more preferably from 0.0001 to 10% by weight, even more preferably from 0.0006 to 6% by weight, per 100% by weight of the beverage. Also, the food or beverage of the present invention is taken so that the effective ingredient contained therein may be taken in an amount of from 10 µg to 1 g/kg body weight, preferably from 50 µg to 500 mg/kg body weight, more preferably from 100 µg to 100 mg/kg body weight, per day for human (for instance, adult).

In addition, the present invention provides a feed for an organism having neuronal protection action, suppressive action for NO production, inhibitory action for aldose reductase or suppressive action for interleukin production, comprising the above-mentioned effective ingredient. In still another embodiment, the present invention also provides a method of feeding an organism, characterized by administering the above-mentioned effective ingredient to the organism. In still yet another embodiment, the present invention provides an organism feeding agent characterized in that the organism feeding agent comprises the above-mentioned effective ingredient. The term "comprise(comprising)" as used herein means contain(containing), add(adding), and/or dilute (diluting) as mentioned above.

In these inventions, the organisms are, for instance, culturing or breeding animals, pet animals, and the like. The culturing or breeding animal is exemplified by cattle, laboratory animals, poultry, pisces, crustaceae or shellfish. The feed is exemplified by a feed for sustenance of and/or amelioration in physical conditioning. The organism feeding agent is exemplified by immersion agents, feed additives, and beverage additives.

According to these inventions, the same effects can be expected to be exhibited as those of the above-mentioned therapeutic agent or prophylactic agent of the present invention, on the basis of the neuronal protection action, suppressive action for NO production, inhibitory action for aldose reductase or suppressive action for interleukin production of the above-mentioned effective ingredient usable in the present invention, in the organism exemplified above for applying these. In other words, the feed or the organism feeding agent of the present invention has a therapeutic or prophylactic effect for a disease requiring neuronal protection, suppression for NO production, inhibition for aldose reductase or suppression for interleukin production in the organism to which the feed or organism feeding agent is applied.

The above-mentioned effective ingredient usable in the present invention is usually administered in an amount of from 10 µg to 1 g/1 kg body weight, preferably from 50 µg to 500 mg/1 kg body weight, more preferably from 100 µg to 100 mg/1 kg body weight to the subject organism, per day. The administration can be made by previously adding and mixing the effective ingredient of the present invention in a raw material for an artificially formulated feed to be given to a subject organism, or mixing the effective ingredient of the present invention with a powder raw material for an artificially formulated feed, and thereafter further adding and mixing the mixture with other raw materials. The content of the above-mentioned effective ingredient in the feed is not particularly limited. The content can be appropriately set in accordance with its purposes, and the content is in a ratio of preferably from 0.001 to 15% by weight.

The process for preparing the feed according to the present invention is not particularly limited, and its composition may be set in accordance with a general feed, as long as the above-mentioned effective ingredient according to the present invention having neuronal protection action, suppressive action for NO production, inhibitory action for aldose reductase or suppressive action for interleukin production may be contained in the feed prepared.

The organism feeding agent may be prepared, used and the like in accordance with the case of the above-mentioned feed.

The organism to which the present invention can be applied is not limited. The culturing or breeding animals include cattle such as *Equus, Bos, Porcus, Ovis, Capra, Camelus*, and *Lama*; experimental animals such as mice, rats, guinea pigs, and rabbits; poultry such as *Chrysolophus*, ducks, *Meleagris*, and *Struthioniformes*; and the pet animals includes dogs, cats, and the like, so that the feed can be widely applied.

By allowing a subject organism to take the feed comprising the above-mentioned effective ingredient usable in the present invention having neuronal protection action, suppressive action for NO production, inhibitory action for aldose reductase or suppressive action for interleukin production, or immersing a subject organism into a solution containing the above-mentioned effective ingredient usable in the present invention having neuronal protection action, suppressive action for NO production, inhibitory action for aldose reductase or suppressive action for interleukin production, the physical conditions of the cattle, experimental animals, poultry, pet animals or the like can be well sustained or ameliorated. The embodiment illustrated herein is one embodiment of the method of feeding an organism provided by the present invention.

In the present invention, the content of the compound of the present invention in the medicament, foodstuff or feed may be at a level so as to give the desired effects in a living body by its administration, intake or the like. It is desired that the compound is contained in an amount higher than the content of the compound of the present invention in usual foodstuff or the like.

No toxicity is found in an oral administration of the mouse of the compound of the present invention or a salt thereof usable in the present invention.

EXAMPLES

The present invention will be described more concretely hereinbelow by means of the examples, but the present invention is by no means limited to these descriptions.

Example 1

Preparation of (E)-1-(5,6,7,8,8a, 10a-hexahydro-1,7-dihydroxy-8,8,10a-trimethyl-9H-xanthen-4-yl)-3-(4-hydroxyphenyl)-2-propen-1-one (1) Twenty-four liters of ethyl acetate was added to 5.8 kg of dry powder of root portions of *Angelica keiskei* koidz., and extraction was carried out with stirring at room temperature for 3 hours. After suction filtration, the mixture was separated into an ethyl acetate extract and residue. After the ethyl acetate extract was concentrated under reduced pressure with a rotary evaporator, the concentrate was dissolved in chloroform, and the entire amount of the solution was absorbed to silica gel BW-300SP (manufactured by Fuji Silysia Chemical Ltd.: 750 ml). Next, the absorbed substances were eluted stepwise with hexane:chloroform=2:5 (750 ml), chloroform (1000 ml), chloroform:methanol=10:1 (1100 ml) in that order.

(2) After the fraction eluted with chloroform:methanol=10:1 obtained in item (1) of Example 1 was concentrated to dryness, the concentrate was dissolved in 30 ml of chloroform. A half the volume of the solution was absorbed to silica gel (BW-300SP, 300 ml). Next, the absorbed substances were eluted stepwise with chloroform (1800 ml), chloroform:methanol=500:7 (300 ml), ethyl acetate (300 ml) in that order.

(3) After the fraction eluted with ethyl acetate obtained in item (2) of Example 1 was concentrated to dryness, the concentrate was dissolved in chloroform:methanol=50:1 (20 ml), and the solution was absorbed to silica gel (BW-300SP, 300 ml). Subsequently, the absorbed substances were eluted stepwise with chloroform:methanol=500:10 (1200 ml), chloroform:methanol=500:13 (500 ml), chloroform:methanol=500:19 (500 ml), chloroform:methanol=500:22 (800 ml), ethyl acetate (500 ml) in that order, and fractions were collected for every 18 ml portion per fraction.

(4) The silica chromato-fractions Nos. 115 to 155 obtained in item (3) of Example 1 were combined, concentrated under reduced pressure, and dissolved in 7 ml of dimethyl sulfoxide. A half the volume of the solution was fractionated by using reversed phase chromatography. As the resin, Cosmosil 140 C18-OPN (manufactured by nakalai tesque Inc.; amount of resin 50 ml) was used. Subsequently, elution was carried out sequentially with distilled water (40 ml), a 20% aqueous ethanol solution (50 ml), a 30% aqueous ethanol solution (50 ml), a 50% aqueous ethanol solution (first-time elution: 50 ml, and then second-time elution: 50 ml), and ethanol (50 ml) in that order.

(5) After 50 ml of the first-time elution portion of the fraction eluted with a 50% aqueous ethanol solution in item (4) of Example 1 was concentrated under reduced pressure, the concentrate was dissolved in 3 ml of a 50% aqueous ethanol solution, and fractionation was carried out by using reversed phase chromatography. The conditions therefor are given below. The column used was TSK gel ODS-80Ts (21.5 mm×30 cm; manufactured by Tosoh Corporation). A solution prepared by mixing distilled water and acetonitrile in a volume ratio of 1:1 was used as a solvent. The elution rate was 5 ml/min., and detection was carried out at 215 nm. Reversed phase chromato-fractions 1 to 5 were collected using ultraviolet absorbance of the eluate as an index.

Figure 1:
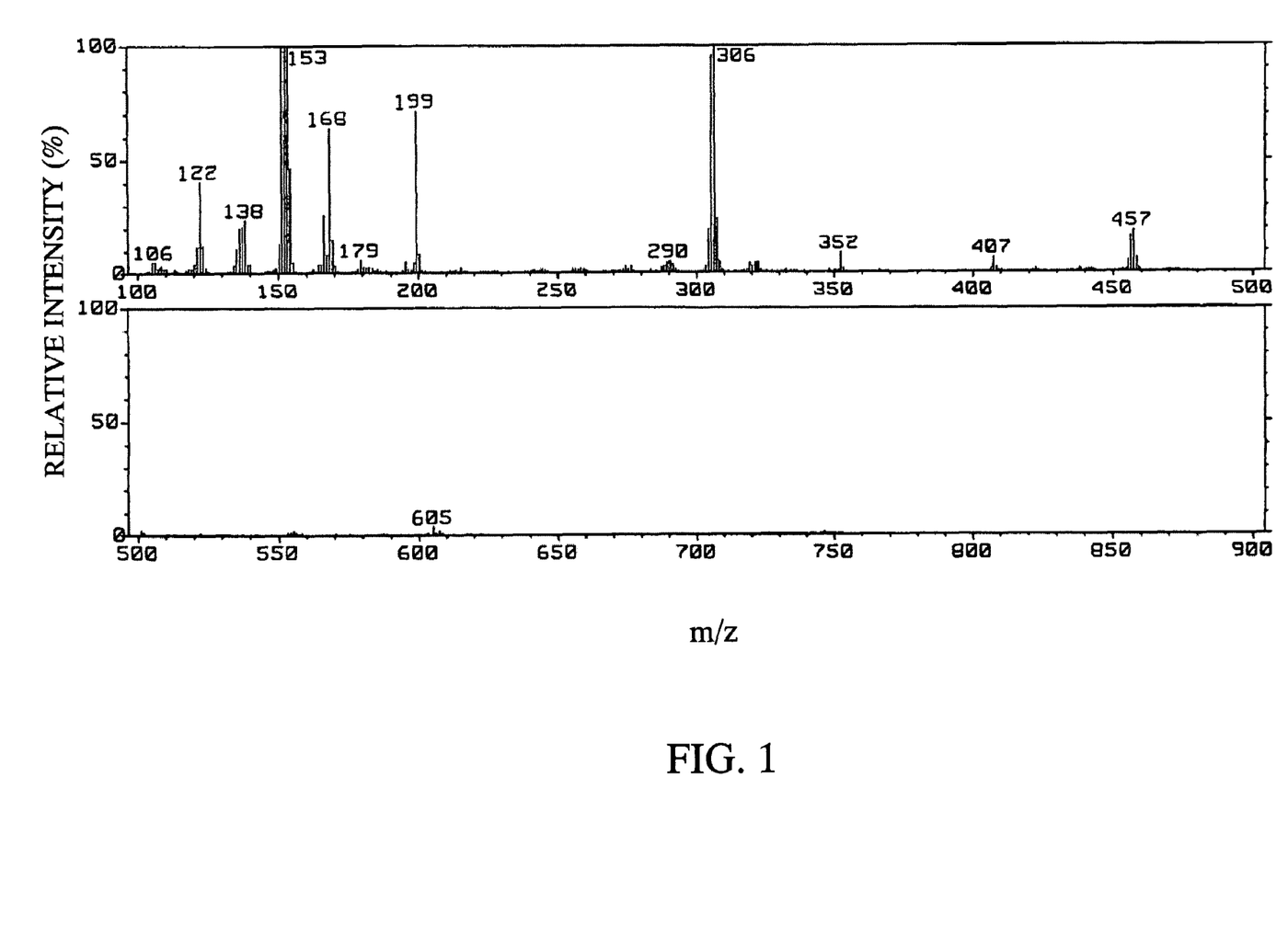

(6) The mass spectrum (MS) of the reversed phase chromato-fraction 2 (a fraction containing a peak detected at a retention time of 24.1 minutes) obtained in item (5) of Example 1 was measured with a mass spectrometer (DX302: manufactured by JEOL LTD.) by FAB-MS technique. As the matrix, m-nitrobenzyl alcohol was used. As a result, a peak of m/z 407(M–H)— was detected. FIG. 1 shows the mass spectrum. In FIG. 1, the axis of abscissas is m/z value, and the axis of ordinates is relative intensity. Next, the structure of the reversed phase chromato-fraction 2 was analyzed by measuring various kinds of NMR spectrum with a nuclear magnetic resonance (NMR) spectrometer (Model AVANCE 600: manufactured by Bruker BIOSPIN). The signals of NMR are shown below. In addition, the numbers of the peaks are shown in the following formula (C).

(C)

¹H-NMR: δ0.81(3H,s,7"-CH₃), 1.03(3H,s,7"-CH₃), 1.25 (3H,s,3"-CH₃), 1.54(1H,m,5"-H), 1.61(1H,dd,J=4.8,13.2 Hz,2"-H), 1.71(1H,m,5"-H), 1.75(1H,m,4"-H), 1.87(1H,m, 4"-H), 2.34(1H,dd,J=13.2,16.8 Hz,1"-H), 2.67(1H,dd,J=4.8, 16.8 Hz,1"-H), 3.27(1H,m,6"-H), 4.65(1H,d,J=4.8 Hz,6"-OH), 6.47(1H,d,J=8.4 Hz,5'-H), 6.83(2H,d,J=8.4 Hz,3-H and 5-H), 7.39(1H,d,J=8.4 Hz,6'-H), 7.42(1H,d,J=15.6 Hz,β-H), 7.48 (1H,d,J=15.6 Hz,α-H), 7.51(2H,d,J=8.4 Hz,2-H and 6-H), 9.97(1H,br-s,4-OH), 10.22(1H,br-s,4'-OH)

Figure 2:
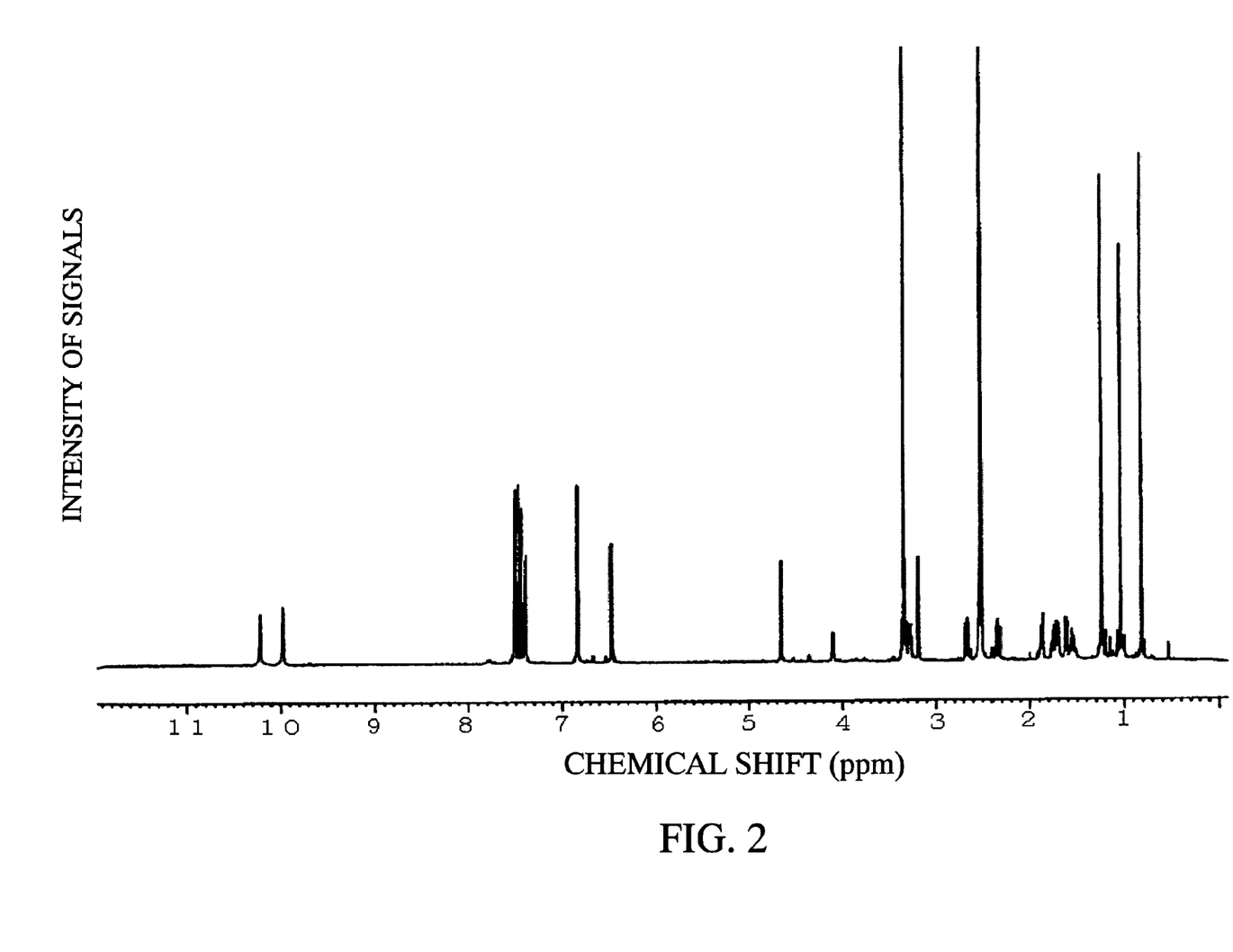

Here, in ¹H-NMR, the sample was dissolved in deuterated dimethyl sulfoxide, and the chemical shift of the residual proton in deuterated dimethyl sulfoxide was expressed as 2.51 ppm. FIG. 2 shows ¹H-NMR spectrum. In FIG. 2, the axis of abscissas is chemical shift, and the axis of ordinates is intensity of signal.

¹³C-NMR: δ 15.3(7"-CH₃), 18.8(1"-C), 20.7(3"-CH₃), 28.1(7"-CH₃), 28.9(5"-C), 38.3(4"-C), 38.9(7"-C), 46.4(2"-C), 76.8(6"-C), 77.9(3"-C), 107.7(5'-C), 110.4(3'-C), 116.8 (3-C and 5-C), 120.8(1'-C), 125.2(α-C), 127.1(1-C), 130.2 (6'-C), 130.8(2-C and 6-C), 141.2(β-C), 154.9(2'-C), 160.3 (4-C), 160.6(4'-C), 189.8(C=O)

Figure 3:
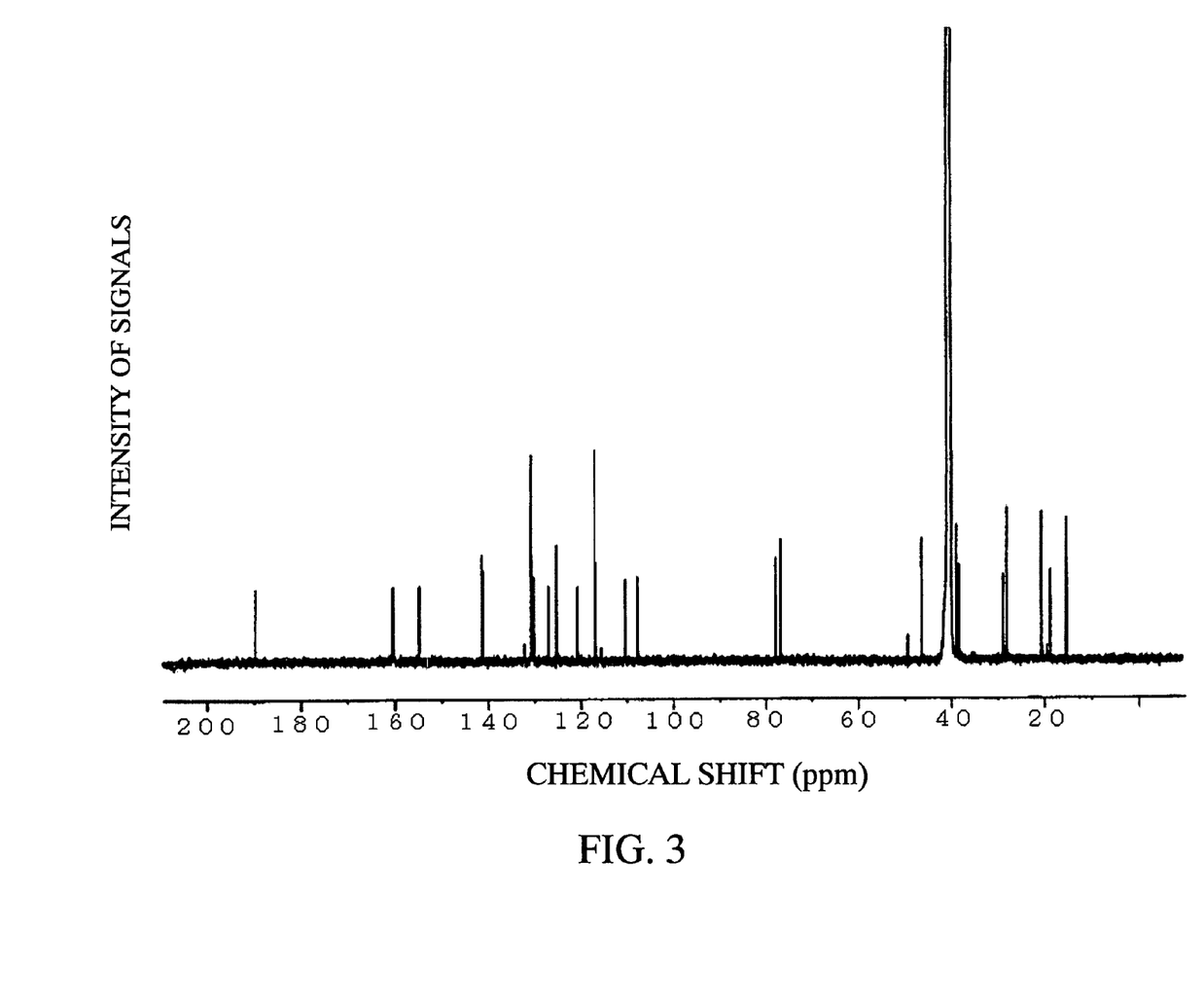

Here, in ¹³C-NMR, the sample was dissolved in deuterated dimethyl sulfoxide, and the chemical shift of deuterated dimethyl sulfoxide was expressed as 40.2 ppm. FIG. 3 shows ¹³C-NMR spectrum. In FIG. 3, the axis of abscissas is chemical shift, and the axis of ordinates is intensity of signal.

From the above results of the mass spectrum analysis and NMR spectrum analysis carried out for the reversed phase chromato-fraction 2, it was confirmed that the reversed phase chromato-fraction 2 is (E)-1-(5,6,7,8,8a,10a-hexahydro-1,7-dihydroxy-8,8,10a-trimethyl-9H-xanthen-4-yl)-3-(4-hydroxyphenyl)-2-propen-1-one (molecular weight: 408, hereinafter referred to as compound a).

Example 2

Figure 4:
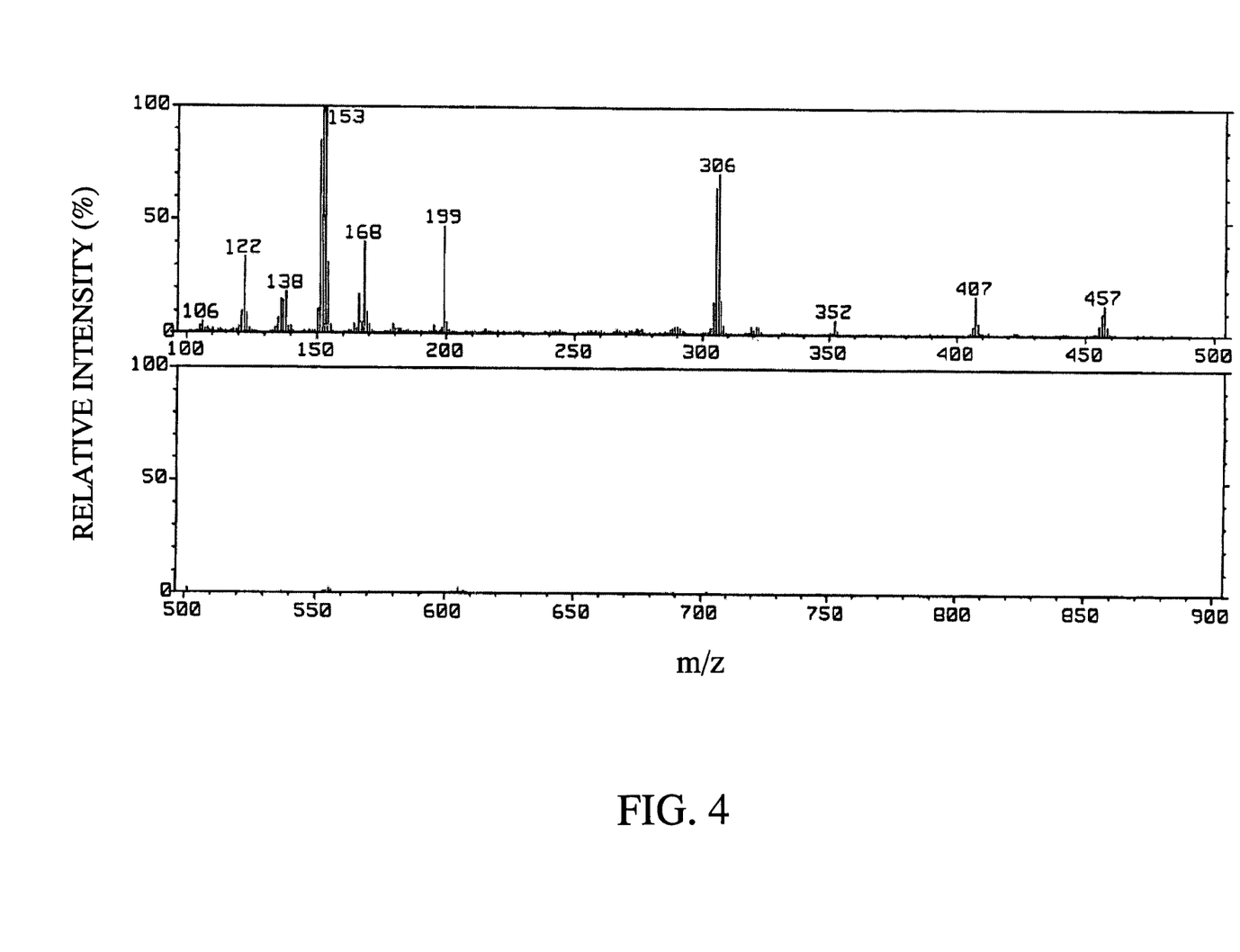
FIG. 4 is a mass spectrum of a compound b.

Preparation of (E)-1-(3,4,-dihydro-3,5-dihydroxy-2-(3-isohexeneyl)-2-methyl-2H-1-benzopyran-8-yl)-3-(4-hydroxyphenyl)-2-propen-1-one (1) The mass spectrum of the reversed phase chromato-fraction 4 (a fraction containing a peak detected at a retention time of 36.2 minutes) obtained in item (5) of Example 1 was measured in the same manner as in item (6) of Example 1. As the matrix, m-nitrobenzyl alcohol was used. A peak of m/z 407(M–H)⁻ was detected with mass spectrometry. FIG. 4 shows the mass spectrum of the reversed phase chromato-fraction 4. In FIG. 4, the axis of abscissas is m/z value, and the axis of ordinates is relative intensity. Next, the NMR spectrum of the reversed phase chromato-fraction 4 was measured in the same manner as in item (6) of Example 1. The signals of NMR are shown below. In addition, the numbers of peaks are shown in the following formula (D).

(D)

¹H-NMR: δ 1.20(3H,s,3"-CH₃), 1.36 (3H,s,7"-CH₃), 1.57 (3H,s,7"-CH₃), 1.68(2H,m,4"-H), 2.10(2H,m,5"-H), 2.41 (1H,dd,J=9.0,16.8 Hz,1"-H), 2.85(1H,dd,J=6.0, 16.8 Hz,1"-H), 3.76(1H,m,2"-H), 5.01(1H,m,6"-H), 5.23(1H,d,J=4.8 Hz,2"-OH), 6.47(1H,d,J=8.4 Hz,5'-H), 6.80(2H,d,J=8.4 Hz,3-H and 5-H), 7.38(1H,d,J=8.4 Hz,6'-H), 7.44(1H,d, J=15.6 Hz,β-H), 7.47(1H,d,J=15.6 Hz,α-H), 7.50(2H,d, J=8.4 Hz,2-H and 6-H), 9.96(1H,s,4-OH), 10.19(1H,s,4'-OH)

Figure 5:
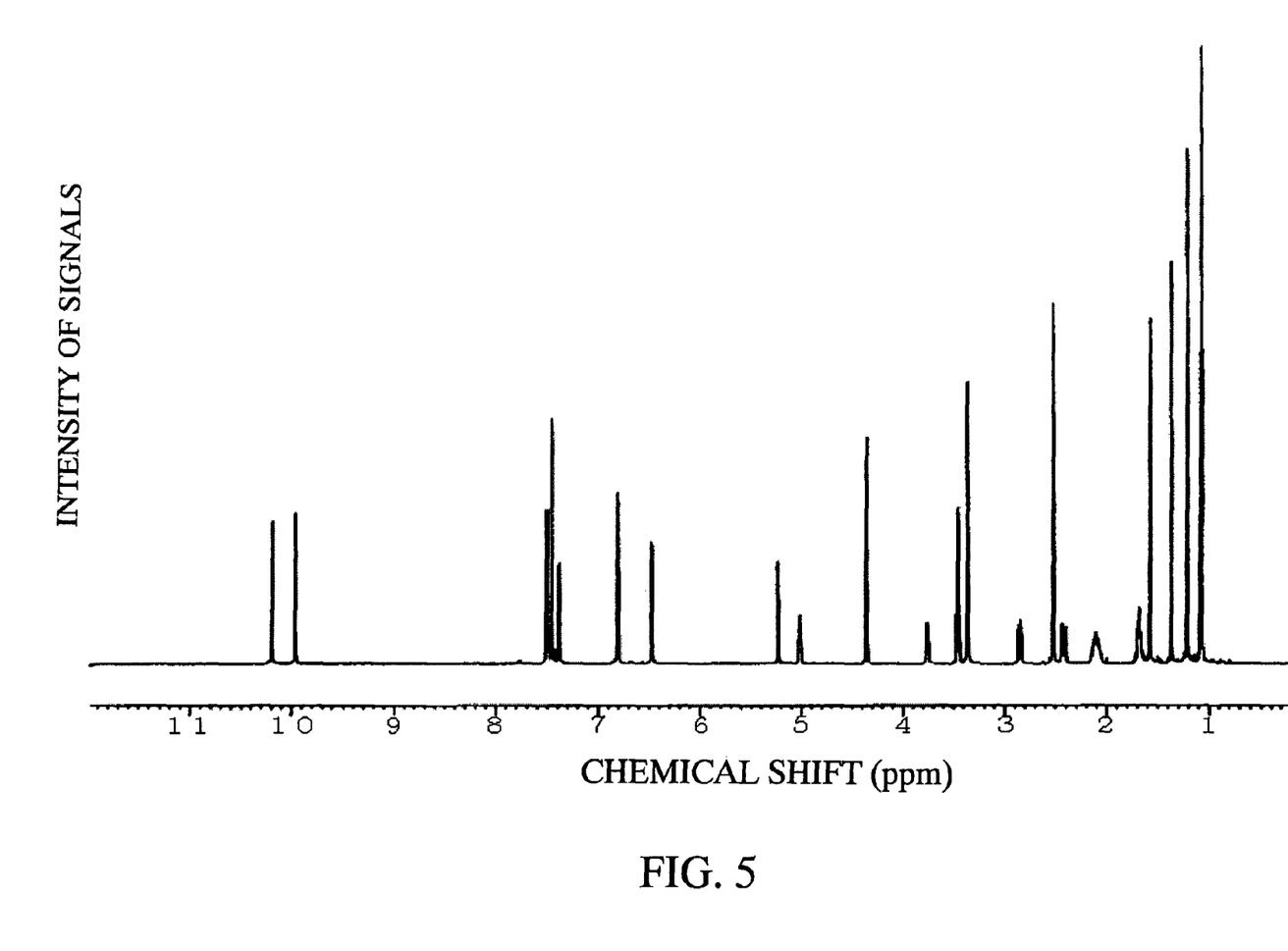
FIG. 5 is a $^1$H-NMR spectrum of the compound b.

Here, in ¹H-NMR, the sample was dissolved in deuterated dimethyl sulfoxide, and the chemical shift of the residual proton in deuterated dimethyl sulfoxide was expressed as 2.51 ppm. FIG. 5 shows ¹H-NMR spectrum of the reversed phase chromato-fraction 4. In FIG. 5, the axis of abscissas is chemical shift, and the axis of ordinates is intensity of signal.

¹³C-NMR: δ 18.1(3"-CH₃), 18.2(7"-CH₃), 22.1(5"-C), 26.3(7"-CH₃), 27.2(1"-C), 38.7(4"-C), 66.7(2"-C), 80.2(3"-C), 107.8(5'-C), 109.1(3'-C), 116.7(3-C and 5-C), 121.0(1'-C), 125.1(6"-C), 125.1(α-C), 127.0(1-C), 130.3(6'-C), 130.8 (2-C and 6-C), 131.6(7"-C), 141.5(β-C),154.6(2'-C), 160.4 (4-C), 160.4(4'-C), 189.9(C=O)

Figure 6:
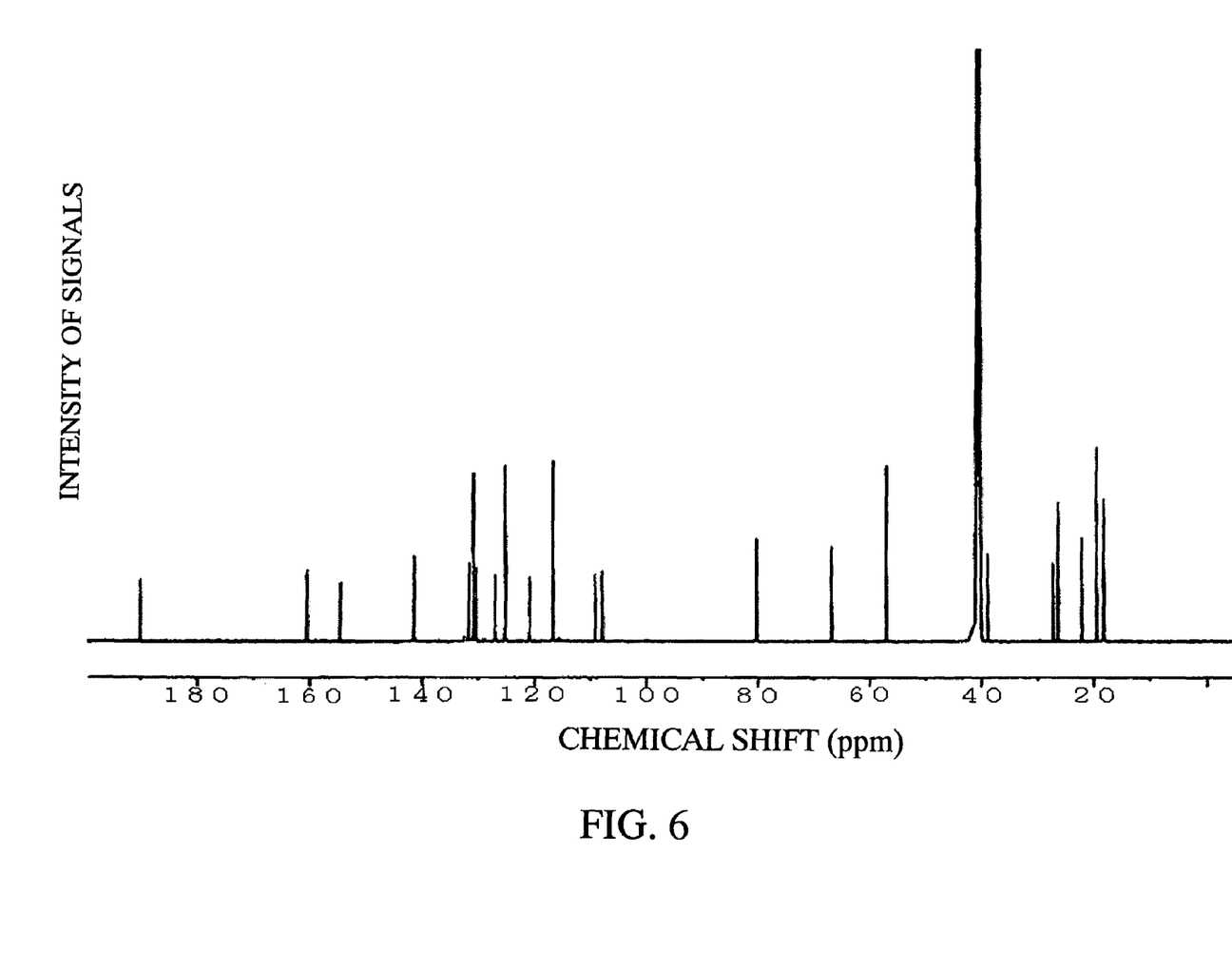
FIG. 6 is a $^{13}$C-NMR spectrum of the compound b.

Here, in ¹³C-NMR, the sample was dissolved in deuterated dimethyl sulfoxide, and the chemical shift of deuterated dimethyl sulfoxide was expressed as 40.2 ppm. FIG. 6 shows ¹³C-NMR spectrum of the reversed phase chromato-fraction 4. In FIG. 6, the axis of abscissas is chemical shift, and the axis of ordinates is intensity of signal.

From the above results of the mass spectrum analysis and NMR spectrum analysis carried out for the reversed phase chromato-fraction 4, it was confirmed that the reversed phase chromato-fraction 4 is (E)-1-(3,4,-dihydro-3,5-dihydroxy-2-(3-isohexeneyl)-2-methyl-2H-1-benzopyran-8-yl)-3-(4-hydroxyphenyl)-2-propene-1-one (molecular weight: 408, hereinafter referred to as compound b).

Example 3

Inhibitory Activities for Aldose Reductase (AR) of Compound a, Compound b (1) Inhibitory activities for aldose reductase of the compounds a and b were measured by the following method. Twenty microliters of 100 mM methylglyoxal was added to 10 µl of the compound a or b (dissolved in a 50% aqueous dimethyl sulfoxide solution) as a sample, 100 µl of 0.2 M phosphate buffer (pH 6.2), 20 µl of 1 mM NADPH (phosphate buffer), 10 µl of a solution of aldose reductase derived from human muscle cells (0.1 U/ml, manufactured by Wako Pure Chemical Industries, phosphate buffer). After 30 seconds passed, change in absorbance of NADPH at 340 nm was determined for 180 seconds. A 50% aqueous dimethyl sulfoxide solution was used as a negative control in place of the sample. In addition, the absorbance was determined using distilled water as a blank of each sample in place of the methylglyoxal solution. The found values are expressed as an average of the values in two experimental values. The inhibitory ratio (%) for aldose reductase was calculated in accordance with the following formula.

Inhibitory Ratio (%)=[1-[($\Delta As-\Delta Asb$)/($\Delta Ac-\Delta Acb$)]]×100

Here, $\Delta As$ and $\Delta Ac$ are changes in absorbance per 1 minute of a sample solution, and a negative control solution, respectively, and $\Delta Asb$ and $\Delta Acb$ are changes in absorbance per 1 minute of blank of a sample solution, and a negative control solution, respectively.

The final concentrations of the amount of the compounds a and b are defined as shown in Table 1. As a result, it was revealed that the compounds a and b have inhibitory activities for aldose reductase in a concentration-dependent manner. The results are shown in Table 1.

TABLE 1

| | Inhibitory Ratio (%) for Aldose Reductase | | | |
|---|---|---|---|---|
| | 2.5 µM | 5 µM | 10 µM | 20 µM |
| Compound a | 33.3 | 48.4 | 65.7 | 77.2 |
| Compound b | 35.1 | 50.6 | 66.8 | 79.1 |

Example 4

Activity for Neuronal Protection of Compound b from Nitrogen Monoxide (NO) Toxicity (1) The suppressive activity for NO toxicity of the compound b was assayed in accordance with the following method. PC12 cells (CRL-1721) derived from rat adrenal medulla pheochromocytoma were suspended in DMEM medium (manufactured by Bio Whittaker) containing 10% fetal bovine serum (manufactured by Bio Whittaker) so as to have a concentration of $1\times10^5$ cells/ml. The suspension was put in each well of a 96-well plate in an amount of 0.1 ml per well, and the cells were cultured at 37° C. in the presence of 5% carbon dioxide gas. After the cells were cultured for 24 hours, the medium was removed and exchanged with DMEM medium containing 10 ng/ml of NGF (manufactured by TAKARA BIO Inc.) and 10% fetal bovine serum. PC12 cells were cultured for 3 days, and differentiated into neuron-like cells. After the culture, the medium was removed and exchanged with DMEM medium containing 10 µM of the compound b, 10 ng/ml of NGF, and 10% fetal bovine serum. After the cells were cultured for 2 hours, sodium nitroprusside (manufactured by nakalai tesque Inc., hereinafter referred to as SNP) was added thereto so as to have a concentration of 50 µM, and the cells were cultured for 48 hours. After the termination of the culture, the medium was removed, and 50 µl of 0.5 mg/ml of MTT (manufactured by nakalai tesque Inc., PBS solution) was added thereto. The cells were cultured for 4 hours. To each well was added 150 µl of dimethyl sulfoxide, and mixed. Solubilized formazan was determined at a wavelength of 590 nm (control wavelength of 630 nm). All of the determinations were carried out twice. Viability ratio (%) of cells was calculated from MTT found values of each test group by defining the MTT value of the control group (group not containing the compound b and SNP) as 100. As a result, it was revealed that the compound b has a suppressive activity for cytotoxicity induced by SNP. The results are shown in Table 2.

TABLE 2

| Test Group | | |
|---|---|---|
| with Addition of SNP | with Addition of Compound b | Viability Ratio (%) of Cells |
| − | − | 100 |
| + | − | 59.1 |
| + | + | 87.4 |

(2) The suppressive activity of the compound b for NO toxicity was assayed in accordance with the following method. PC12 cells derived from rat adrenal medulla pheochromocytoma were suspended in DMEM medium containing 10% fetal bovine serum so as to have a concentration of $1.5\times10^5$ cells/ml. The suspension was put to each well of a 96-well plate in an amount of 0.1 ml per well, and cultured at 37° C. in the presence of 5% carbon dioxide gas. After 24 hours of culture, the medium was removed, and exchanged with DMEM medium containing 10 µM of the compound b and 10% fetal bovine serum. After the cells were cultured for 2 hours, SNP was added thereto so as to have a concentration of 50 µM, and the cells were cultured for 66 hours. After the termination of the culture, the MTT determination was carried out in the same manner as in item (1) of Example 4, and the viability ratio (%) of cells was calculated. All of the determinations were carried out three times. As a result, it was revealed that the compound b has a suppressive activity for cytotoxicity induced by SNP. The results are shown in Table 3.

TABLE 3

| Test Group | | |
|---|---|---|
| with Addition of SNP | with Addition of Compound b | Viability Ratio (%) of Cells |
| − | − | 100 |
| + | − | 48.1 |
| + | + | 91.0 |

Example 5

Suppressive Activities for NO Production of Compound a and Compound b

Figure 7:
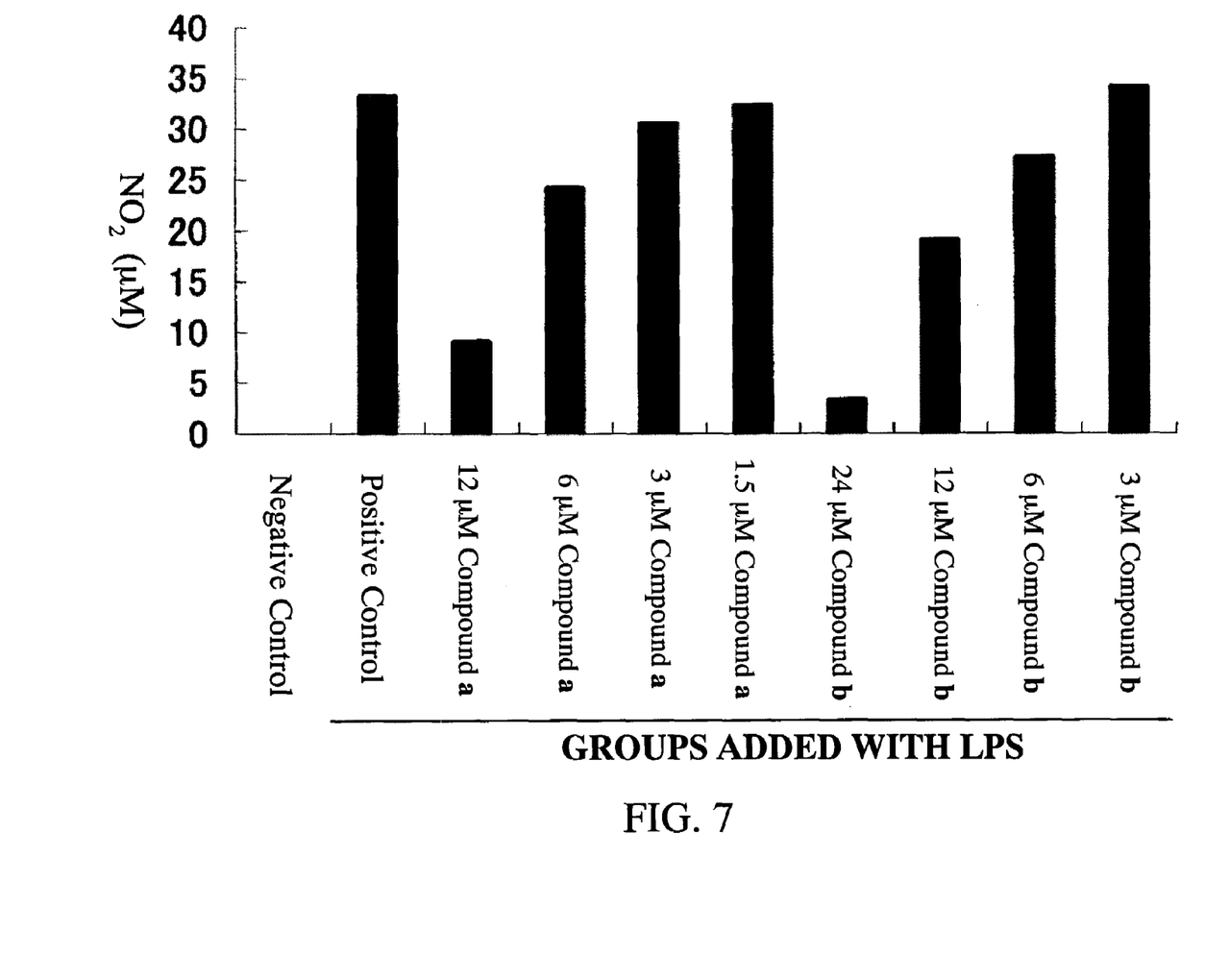
FIG. 7 is a diagram showing a suppressive action for NO production by the compound a or the compound b.

RAW 264.7 cells (ATCC TIB 71) were suspended in Dulbecco's modified Eagle's medium (manufactured by Bio Whittaker, 12-604F) containing 10% fetal bovine serum (manufactured by GIBCO), so as to have a concentration of $4\times10^5$ cells/ml, and the suspension was put to each well of a 48-well microtiter plate in an amount of 500 μl per well. The cells were cultured at 37° C. in the presence of 5% carbon dioxide gas. After 24 hours, the medium was exchanged with Dulbecco's modified Eagle's medium (manufactured by Bio Whittaker, 12-917F) containing 10% fetal bovine serum (manufactured by GIBCO), 2 mM L-glutamine (manufactured by Life Tech Oriental Co., Ltd., 25030-149) without containing phenol red. The compound a (dimethyl sulfoxide solution) was added to each well so as to have a concentration of 1.5, 3, 6, or 12 μM, or the compound b (dimethyl sulfoxide solution) was added to each well so as to have a concentration of 3, 6, 12, or 24 μM. After additional 1 hour of culture, a 100 μg/ml aqueous lipopolysaccharide (LPS, manufactured by Sigma, L-2010) solution was added to each well in an amount of 511 per well, and the cells were cultured for 15 hours. Thereafter, the concentration of $NO_2^-$ which was produced by oxidation of NO in the medium was determined. In addition, there were set a group without addition of the compounds a and b as a positive control, and a group without addition of LPS as a negative control. After above-mentioned culture, 100 μl of a 4% grease reagent (manufactured by Sigma, G4410) was added to 100 μl of the supernatant of the culture medium, and the mixture was allowed to stand at room temperature for 15 minutes. Thereafter, absorbance at 540 nm was determined. The concentration of $NO_2$ _ in the medium was calculated from a calibration curve prepared from known concentrations of $NaNO_2$. All of the determinations were carried out twice. As a result, both the group with addition of the compound a and the group with addition of the compound b supppressed the induction for NO production by LPS in a concentration-dependent manner. The results are shown in FIG. 7. In other words, FIG. 7 shows the concentration of $NO_2^-$ in the culture medium. In FIG. 7, the axis of abscissas is each sample, and the axis of ordinates is concentrations of $NO_2^-$ (μM).

Example 6

Suppressive Activities for IL-6 Production of Compound a and Compound b

Figure 8:
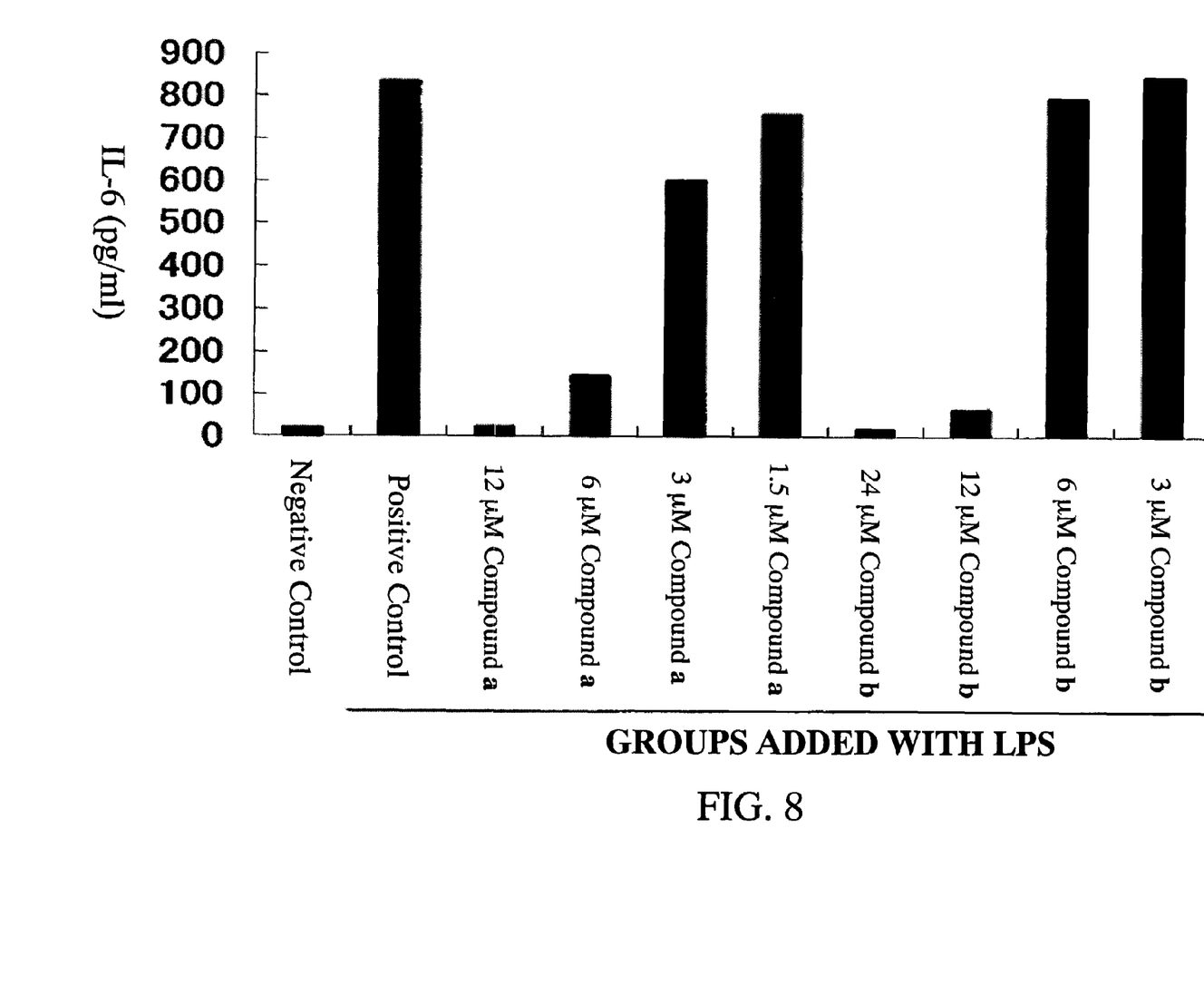
FIG. 8 is a diagram showing a suppressive action for IL-6 production by the compound a or the compound b.

RAW 264.7 cells (ATCC TIB 71) were suspended in Dulbecco's modified Eagle's medium (manufactured by Bio Whittaker, 12-604F) containing 10% fetal bovine serum (manufactured by GIBCO) so as to have a concentration of $4\times10^5$ cells/ml, and the suspension was put to each well of a 48-well microtiter plate in an amount of 500 μl per well. The cells were cultured at 37° C. in the presence of 5% carbon dioxide gas. After 24 hours, the medium was exchanged with Ultra CHO medium (manufactured by Bio Whittaker, 12-724Q). The compound a (dimethyl sulfoxide solution) was added to each well so as to have a concentration of 1.5, 3, 6, or 12 μM, or the compound b (dimethyl sulfoxide solution) was added to each well so as to have a concentration of 3, 6, 12, or 24 μM. After additional 4 hours of culture, a 100 μg/ml aqueous lipopolysaccharide (LPS, manufactured by Sigma, L-2010) solution was added to each well in an amount of 5 μl per well, and the cells were cultured for 15 hours. Thereafter, the supernatant of the medium was collected. The content of interleukin 6 (IL-6) in the supernatant of the medium was determined with a sandwich enzyme immunoassay (manufactured by genzyme TECHNE, 4922). In addition, there were set a group without addition of the compounds a and b as a positive control, and a group without addition of LPS as a negative control. All of the determinations were carried out twice. As a result, both the group with addition of the compound a and the group with addition of the compound b inhibited the induction of IL-6 production by LPS in a concentration-dependent manner. The results are shown in FIG. 8. In other words, FIG. 8 shows the concentration of IL-6 (pg/ml) in the supernatant of the culture medium. In FIG. 8, the axis of abscissas is each sample, and the axis of ordinates is the concentration of IL-6 (pg/ml).

INDUSTRIAL APPLICABILITY

According to the present invention, a novel chalcone compound is provided. The compound has a neuronal protection action, a suppressive action for NO production, an inhibitory action for aldose reductase or a suppressive action for interleukin production, and the compound is useful as a medicament, food, beverage, or feed utilizing the physiological activities.

The invention claimed is:

1. A compound represented by the following general formula (1):

wherein $R_1$ and $R_2$ are taken together with the carbon atom to which they are bound, respectively, to form a hydroxydimethyl cyclohexane ring, or where $R_1$ is a hydroxyl group, $R_2$ is an isohexenyl group,
an ester, ether or glycoside prodrug thereof, or a salt thereof.

2. A therapeutic agent wherein the agent comprises the compound according to claim 1 as an effective ingredient.

3. A method of protecting neurons from nitrogen monoxide (NO) toxicity, suppressing nitrogen monoxide (NO) production, inhibiting aldose reductase or suppressing interleukin-6 production, wherein said method comprises:

Administering an effective amount of the therapeutic agent, according to claim 2, to a subject in need thereof.

4. A food, beverage or feed wherein the food, beverage or feed, comprises the compound as defined in claim 1.

5. The method according to claim 3, wherein the therapeutic agent is administered in a food, beverage or feed to a subject in need thereof.

* * * * *